(12) United States Patent
Melakari et al.

(10) Patent No.: US 12,105,873 B2
(45) Date of Patent: Oct. 1, 2024

(54) LIGHT FIELD BASED EYE TRACKING

(71) Applicant: Pixieray Oy, Espoo (FI)

(72) Inventors: Klaus Melakari, Espoo (FI); Semih Iseri, Helsinki (FI); Ari Pitkänen, Vantaa (FI)

(73) Assignee: Pixieray Oy, Espoo (FI)

( * ) Notice: Subject to any disclaimer, the term of this patent is extended or adjusted under 35 U.S.C. 154(b) by 196 days.

(21) Appl. No.: 18/071,067

(22) Filed: Nov. 29, 2022

(65) Prior Publication Data
US 2024/0176415 A1   May 30, 2024

(51) Int. Cl.
| | | |
|---|---|---|
| *G06F 3/01* | (2006.01) | |
| *A61B 3/00* | (2006.01) | |
| *A61B 3/113* | (2006.01) | |
| *G06V 40/19* | (2022.01) | |
| *A61B 17/00* | (2006.01) | |

(52) U.S. Cl.
CPC ............ *G06F 3/013* (2013.01); *A61B 3/0008* (2013.01); *A61B 3/113* (2013.01); *G06V 40/19* (2022.01); *A61B 2017/00057* (2013.01)

(58) Field of Classification Search
CPC ......... G06V 40/19; G06F 3/013; A61B 3/113; A61B 3/0008; A61B 2017/00057; A61B 2017/00216; A61F 9/023; G02B 27/0172; G02C 7/10
See application file for complete search history.

(56) References Cited

U.S. PATENT DOCUMENTS

| | | | | |
|---|---|---|---|---|
| 9,846,307 | B2* | 12/2017 | Tremblay | G02B 26/0833 |
| 10,032,074 | B2* | 7/2018 | Publicover | H04N 23/90 |
| 10,281,745 | B2* | 5/2019 | Knoll | A61F 9/023 |
| 10,395,111 | B2* | 8/2019 | Konttori | G02B 5/30 |
| 10,444,545 | B2* | 10/2019 | Knoll | G02C 11/04 |
| 10,452,911 | B2* | 10/2019 | Ollila | G06F 3/013 |
| 10,613,352 | B2* | 4/2020 | Knoll | G02C 7/101 |
| 11,971,542 | B2* | 4/2024 | Vlaskamp | G02B 27/0172 |
| 2006/0028400 | A1* | 2/2006 | Lapstun | G02B 27/0093 |
| | | | | 345/8 |
| 2010/0149073 | A1* | 6/2010 | Chaum | G02B 27/0075 |
| | | | | 345/8 |
| 2015/0085251 | A1* | 3/2015 | Larsen | G06F 3/013 |
| | | | | 351/206 |

(Continued)

*Primary Examiner* — Olga V Merkoulova
(74) *Attorney, Agent, or Firm* — Ziegler IP Law Group LLC.

(57) ABSTRACT

An eye-tracking system includes light-sensing units, each light-sensing unit including at least three light sensors and converging lens to converge light signals towards one or more of at least three light sensors; and processor(s) configured to: collect sensor data from individual light sensors, sensor data being indicative of respective light intensities of light signals sensed by individual light sensors; determine direction from which light signals are incident upon light-sensing unit, based on differences in light intensities of light signals; determine orientation of user's eye relative to given light-sensing unit, based on direction from which light signals are incident upon light-sensing unit and light intensities of light signals; and determine gaze direction of user's eye, based on orientation of user's eye and position of light-sensing unit relative to user's eye.

17 Claims, 5 Drawing Sheets

(56) References Cited

U.S. PATENT DOCUMENTS

| | | | | |
|---|---|---|---|---|
| 2016/0033771 A1* | 2/2016 | Tremblay | ............... | G02B 26/10 |
| | | | | 359/851 |
| 2016/0363995 A1* | 12/2016 | Rougeaux | ............... | G02B 26/06 |
| 2017/0116476 A1* | 4/2017 | Publicover | ............. | H04N 23/56 |
| 2017/0199396 A1* | 7/2017 | Knoll | ...................... | G02C 7/101 |
| 2018/0157908 A1* | 6/2018 | Sahlsten | ............ | G02B 27/0172 |
| 2018/0235465 A1* | 8/2018 | Calpe Maravilla | ....... | G06T 7/13 |
| 2019/0019023 A1* | 1/2019 | Konttori | ............. | G02B 27/017 |
| 2019/0219844 A1* | 7/2019 | Knoll | ...................... | A61F 9/023 |
| 2019/0236355 A1* | 8/2019 | Ollila | ..................... | G06V 40/19 |
| 2019/0311527 A1* | 10/2019 | Schwab | ............ | G02B 27/0093 |
| 2019/0324276 A1* | 10/2019 | Edwin | .................... | G06V 20/20 |
| 2019/0391413 A1* | 12/2019 | Knoll | ...................... | G02C 11/04 |
| 2020/0043236 A1* | 2/2020 | Miller | ................... | G06T 19/006 |
| 2021/0133994 A1* | 5/2021 | Valli | ..................... | G02B 27/017 |
| 2021/0373327 A1* | 12/2021 | Vlaskamp | .......... | G02B 27/0093 |
| 2024/0036310 A1* | 2/2024 | Melakari | ............ | G02B 27/0101 |
| 2024/0176415 A1* | 5/2024 | Melakari | ................ | G06V 40/19 |

* cited by examiner

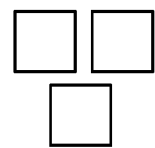 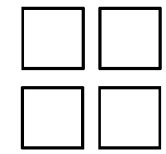
FIG. 4A  FIG. 4B
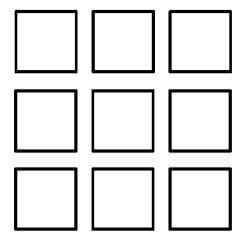 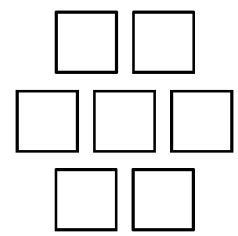
FIG. 4C  FIG. 4D
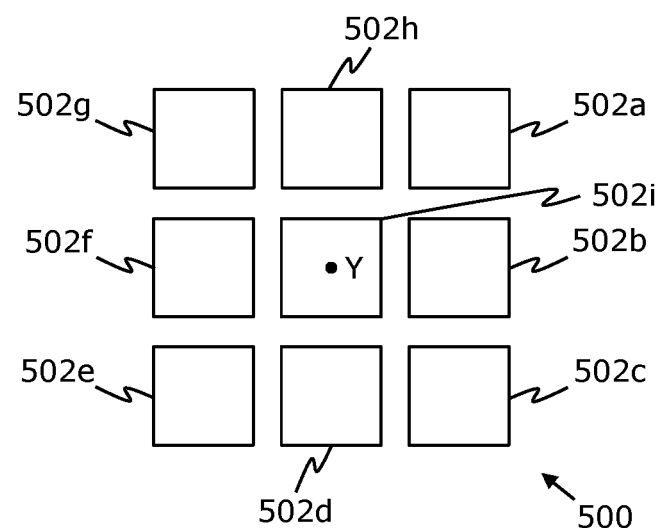
FIG. 5

LIGHT FIELD BASED EYE TRACKING

TECHNICAL FIELD

The present disclosure relates to eye-tracking systems. The present disclosure also relates to apparatuses implementing such eye-tracking systems. The present disclosure further relates to methods for eye tracking.

BACKGROUND

In recent times, there has been rapid advancements in eye-tracking technology. Generally, the eye-tracking technology employs eye-tracking systems that detect and/or track a user's gaze within a visual scene in real time or near-real time. Such eye-tracking systems are being employed in various fields, such as immersive technologies, entertainment, medical imaging operations, simulators, navigation, and the like.

However, existing eye-tracking systems and methods for eye tracking are associated with several limitations. Firstly, some existing eye-tracking systems and methods employ one or more cameras to capture images of a user's eye, and process the captured images to track the user's gaze. These cameras could be visible-light cameras, infrared cameras, Shack-Hartman sensors-based light-field cameras, or similar. However, camera-based eye-tracking systems are not only expensive to manufacture, but also require heavy computational processing. Secondly, some other existing eye-tracking systems and methods employ light sensors to track a user's eye by sensing reflections of light off the user's eye. Often, such reflections also include unwanted reflections, for example, due to features (for example, eyelids, eyelashes, epicanthic folds, and the like) of the user's eye as well as other areas of an eye socket of the user's eye. In such a case, a signal-to-noise ratio for the reflections is significantly reduced and reflections that are useful for eye-tracking purposes are very difficult to differentiate from unwanted reflections. Thus, even when the processing of such reflections utilises significant computational resources and time, the results may still be inaccurate. Thirdly, such light-sensor-based eye-tracking systems are not well-suited for accurately tracking eyes of different users. This is because exact locations of eyes of the different users may change as the different users have different eye configurations (for example, such as different vertex distances, different interpupillary distances, different sizes and/or shapes of eye sockets, and the like). As a result, eye tracking for the different users is highly error-prone and unreliable. Moreover, even for a same person, the eye-tracking system may move in relation to the eyes during use; any such movement has a negative effect on the accuracy of eye tracking, thereby reducing the reliability of such eye-tracking systems.

Therefore, in light of the foregoing discussion, there exists a need to overcome the aforementioned drawbacks associated with existing eye-tracking systems and methods for eye tracking.

SUMMARY

The present disclosure seeks to provide an eye-tracking system. The present disclosure also seeks to provide an apparatus implementing such an eye-tracking system. The present disclosure further seeks to provide a method for eye tracking. An aim of the present disclosure is to provide a solution that overcomes at least partially the problems encountered in prior art.

In a first aspect, an embodiment of the present disclosure provides an eye-tracking system comprising:
a plurality of light-sensing units, each light-sensing unit comprising at least three light sensors and a converging lens employed to converge light signals incident thereupon towards one or more of the at least three light sensors; and
at least one processor configured to:
collect sensor data from individual light sensors of a given light-sensing unit at a given instant of time, the sensor data being indicative of respective light intensities of the light signals sensed by the individual light sensors;
determine a direction from which the light signals are incident upon the given light-sensing unit at the given instant of time, based on differences in the respective light intensities of the light signals sensed by the individual light sensors;
determine an orientation of a user's eye relative to the given light-sensing unit at the given instant of time, based on the direction from which the light signals are incident upon the given light-sensing unit and the light intensities of the light signals sensed by the individual light sensors; and
determine a gaze direction of the user's eye at the given instant of time, based on the orientation of the user's eye relative to the given light-sensing unit and a position of the given light-sensing unit relative to the user's eye.

In a second aspect, an embodiment of the present disclosure provides an apparatus implementing the eye-tracking system of the first aspect, comprising at least one lens, wherein a first surface of the at least one lens is to face the user's eye when the apparatus is used by the user, wherein the plurality of light-sensing units are arranged along or in proximity of a periphery of the first surface of the at least one lens.

In a third aspect, an embodiment of the present disclosure provides a method for eye-tracking using an eye-tracking system comprising a plurality of light-sensing units, each light-sensing unit comprising at least three light sensors and a converging lens employed to converge light signals incident thereupon towards one or more of the at least three light sensors, the method comprising:
collecting sensor data from individual light sensors of a given light-sensing unit at a given instant of time, the sensor data being indicative of respective light intensities of the light signals sensed by the individual light sensors;
determining a direction from which the light signals are incident upon the given light-sensing unit at the given instant of time, based on differences in the respective light intensities of the light signals sensed by the individual light sensors;
determining an orientation of a user's eye relative to the given light-sensing unit at the given instant of time, based on the direction from which the light signals are incident upon the given light-sensing unit and the light intensities of the light signals sensed by the individual light sensors; and
determining a gaze direction of the user's eye at the given instant of time, based on the orientation of the user's eye relative to the given light-sensing unit and a position of the given light-sensing unit relative to the user's eye.

Embodiments of the present disclosure substantially eliminate or at least partially address the aforementioned problems in the prior art, and facilitate a simple, yet accurate and reliable way to determine a gaze direction of a user's eye in real time or near-real time by way of light field based eye tracking.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIGS. 4A, 4B, 4C, and 4D illustrate various predefined arrangements in which light sensors of a light-sensing unit can be arranged, in accordance with an embodiment of the present disclosure;

FIG. 5 illustrates an exemplary scenario of determining a direction from which light signals are incident upon a given light-sensing unit, in accordance with an embodiment of the present disclosure;

Figure 1A:
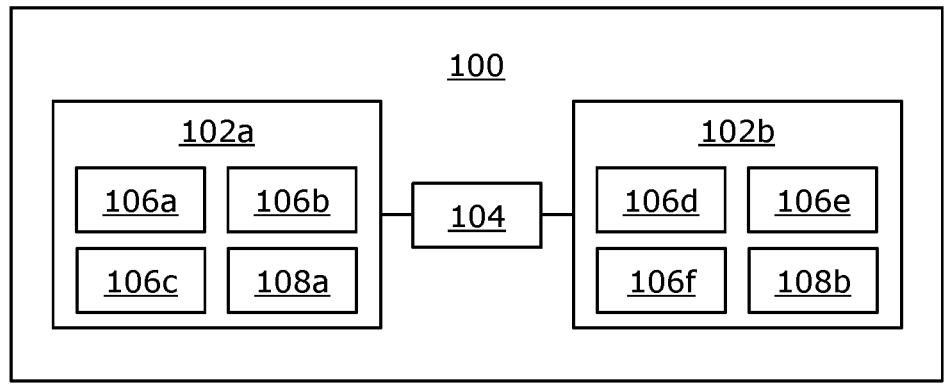
FIGS. 1A and 1B illustrate block diagrams of architectures of an eye-tracking system, in accordance with different embodiments of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In a first aspect, an embodiment of the present disclosure provides an eye-tracking system comprising:
a plurality of light-sensing units, each light-sensing unit comprising at least three light sensors and a converging lens employed to converge light signals incident thereupon towards one or more of the at least three light sensors; and
at least one processor configured to:
collect sensor data from individual light sensors of a given light-sensing unit at a given instant of time, the sensor data being indicative of respective light intensities of the light signals sensed by the individual light sensors;
determine a direction from which the light signals are incident upon the given light-sensing unit at the given instant of time, based on differences in the respective light intensities of the light signals sensed by the individual light sensors;
determine an orientation of a user's eye relative to the given light-sensing unit at the given instant of time, based on the direction from which the light signals are incident upon the given light-sensing unit and the light intensities of the light signals sensed by the individual light sensors; and
determine a gaze direction of the user's eye at the given instant of time, based on the orientation of the user's eye relative to the given light-sensing unit and a position of the given light-sensing unit relative to the user's eye.

In a second aspect, an embodiment of the present disclosure provides an apparatus implementing the eye-tracking system of the first aspect, comprising at least one lens, wherein a first surface of the at least one lens is to face the user's eye when the apparatus is used by the user, wherein the plurality of light-sensing units are arranged along or in proximity of a periphery of the first surface of the at least one lens.

In a third aspect, an embodiment of the present disclosure provides a method for eye-tracking using an eye-tracking system comprising a plurality of light-sensing units, each light-sensing unit comprising at least three light sensors and a converging lens employed to converge light signals incident thereupon towards one or more of the at least three light sensors, the method comprising:
collecting sensor data from individual light sensors of a given light-sensing unit at a given instant of time, the sensor data being indicative of respective light intensities of the light signals sensed by the individual light sensors;
determining a direction from which the light signals are incident upon the given light-sensing unit at the given instant of time, based on differences in the respective light intensities of the light signals sensed by the individual light sensors;
determining an orientation of a user's eye relative to the given light-sensing unit at the given instant of time, based on the direction from which the light signals are incident upon the given light-sensing unit and the light intensities of the light signals sensed by the individual light sensors; and
determining a gaze direction of the user's eye at the given instant of time, based on the orientation of the user's eye relative to the given light-sensing unit and a position of the given light-sensing unit relative to the user's eye.

The present disclosure provides the aforementioned eye-tracking system, the aforementioned apparatus, and the aforementioned method, which facilitate a simple, yet accurate and reliable way to determine a gaze direction of a user's eye, in real time or near-real time by way of light field based eye tracking. Herein, the orientation of the user's eye is determined based on the direction from which the light signals are incident and the light intensities of the light signals, which together represent a light field in a proximity of the user's eye. This allows the gaze direction to be determined with a high accuracy and precision. Moreover, as the eye-tracking method employs light sensors, instead of cameras, it is neither computationally intensive nor time consuming.

The eye-tracking system is susceptible to be implemented in various types of apparatuses, for example, such as head-mounted display devices, eyeglasses, microscopes, telescopes, or similar. Moreover, the eye-tracking system is suitable to be employed for accurately and reliably tracking the gaze of different users having different eye configurations, and is also adaptable to movement of the eye-tracking system in relation to the user's eye during eye tracking.

Throughout the present disclosure, the term "eye-tracking system" refers to a specialized equipment that is employed to detect and/or follow the user's eye for determining the gaze direction of the user's eye. It will be appreciated that the eye-tracking system is arranged in the apparatus in a manner that it does not cause any obstruction in a user's view. Thus, the apparatus utilizes the eye-tracking system for determining the gaze direction of the user's eye via non-invasive techniques. Moreover, an accurate tracking of the gaze direction may facilitate said apparatus to closely implement gaze contingency, for example, such as when presenting an extended-reality (XR) environment to the user, or in case of adaptive eyeglasses. The term "extended-reality" encompasses virtual reality (VR), augmented reality (AR), mixed reality (MR), and the like.

Throughout the present disclosure, the term "light sensor" refers to an equipment that is operable to detect (namely, sense) the light signals incident thereupon. Optionally, a given light sensor is implemented as one of: an infrared (IR) light sensor, a visible light sensor, an ultraviolet (UV) light sensor. Correspondingly, in this regard, the light signals could be one of: IR light signals, visible light signals, UV light signals. In an example implementation, a given light sensor may be implemented as a photodiode. The photodiode may, for example, be made up of silicon, germanium, indium gallium arsenide, mercury cadmium telluride, and the like. Photodiodes can be employed to detect different types of light, for example, such as visible light, infrared, and ultra-violet. Notably, a photodiode produces a larger current when it is exposed to more light. Photodiodes are well-known in the art.

It will be appreciated that greater the number of light sensors in the given light-sensing unit, greater is the accuracy of the eye-tracking system. However, in order to determine the direction from which the light signals are incident upon the given light-sensing unit (hereinafter referred to as the "light direction" for the sake of convenience only) with an acceptable accuracy, a minimum of three light sensors in the given light-sensing unit are preferred to be employed. Moreover, the given light sensor is at least partially sensitive to the light direction, and thus facilitates in determining not only a signal strength of the light signals, but also the direction of a majority of the light signals.

Generally, greater the size of a light-gathering area of a given light sensor, greater is the signal-to-noise ratio. However, for implementation purposes, a size of the given light sensor is a limiting factor. Thus, a light capturing angle for the given light sensor (i.e., an angle of a field within which the given light sensor is capable of sensing the incident light signals) is kept wide enough to ensure that a maximum number of eye positions lie within the light capturing angle. The light capturing angle could be equal to an angular width of a rotational area of an iris of the user's eye (that is, an area within which the iris can be detected even when the iris rotates in different directions). The light capturing angle could be even greater than the angular width of the rotational area of the iris by a few degrees. It will be appreciated that the light capturing angle depends on a distance between the given light sensor and the user's eye.

Throughout the present disclosure, the term "converging lens" refers to an optical element that is capable of converging the light signals incident thereupon towards one or more of the at least three light sensors. Optionally, the converging lens is implemented as one of: a planoconvex lens, a concavo-convex lens, a double convex lens, a biconvex lens. It will be appreciated that the converging lens converges the light signals towards the one or more of the at least three light sensors, based on the light direction relative to an arrangement of the at least three light sensors (which is indicative of an angle of incidence of the light signals).

Notably, the at least one processor controls an overall operation of the eye-tracking system. For this purpose, the at least one processor is at least communicably coupled to the plurality of light-sensing units. It will be appreciated that the at least one processor may include a microcontroller or a microprocessor to control operations of the at least three light sensors.

Notably, when the light signals are incident upon the individual light sensors, the individual light sensors sense the respective light intensities of the light signals for generating the sensor data. The sensor data is generated by the individual light sensors and is collected by the at least one processor in real time or near-real time (without any latency/delay). Light intensity of a given light signal could be expressed, for example, such as in terms of any one of: lumen, footcandle, lux. It is to be understood that, for the given light-sensing unit, when the light signals are incident upon the one or more of the at least three light sensors, the sensor data is indicative of the light intensities of the light signals sensed individually by the one or more of the at least three light sensors.

It will be appreciated that when light intensity of the light signals sensed by a given light sensor from amongst the at least three light sensors is highest, it is likely that the light signals (after being reflected from the user's eye) are incident upon the given light-sensing unit from a direction opposite to a direction in which the given light sensor is arranged relative to a centre of the converging lens. Therefore, the direction from which the light signals are incident upon the given light-sensing unit could be easily determined by the at least one processor using at least one mathematical technique. The at least one mathematical technique could, for example, be a trigonometry-based technique. For example, the light direction could be determined by extending an imaginary line from a centre of the converging lens towards the given light sensor.

In a first example, a light-sensing unit may comprise three light sensors A1, A2, and A3, wherein 15, 70 and 15 percent of the light signals may be incident upon the light sensors A1, A2 and A3, respectively. In such a case, when the light sensor A2 is arranged towards a northwest direction relative to the centre of the converging lens, the light direction may be determined to be from a southeast direction towards the centre of the converging lens. It will be appreciated that this example merely represents the light direction from a two-dimensional perspective of the arrangement of the light sensors in the light-sensing unit; the actual light direction would also take into account a separation distance between the converging lens and the arrangement of the light sensors.

It will be appreciated that when an arrangement of the individual light sensors, and the differences in the respective light intensities of the light signals sensed by the individual light sensors (namely, a correlation of the respective light intensities) are known, the direction from which the light signals are incident upon the given light-sensing unit could be accurately determined by the at least one processor without confusing it with a direction of surrounding light (from the real-world environment). This may, for example, be a case in which a given light sensor may also sense sunlight incoming from the real-world environment, in addition to a red colour signal incoming from a light source. Furthermore, the differences in the respective light intensities could be analysed by the at least one processor for determining a relative correlation strength, and subsequently the direction can be determined. This can be done by not taking into account those light signals whose light intensity is dropping below a pre-defined level (i.e., ignoring those directions from which it is least expected to receive the light signals). In such a case, the relative correlation strength reduces for those sensors that do not receive the light signals well, and the relative correlation strength increases for only sensors that are receiving the light signals well from expected directions. This may be referred to as the digital modulated transmission principle. Techniques for the digital modulated transmission (or even analog modulated transmission) are well-known in the art.

Additionally, optionally, in a case where light sources are employed to emit light signals, different encoding could be used to distinguish between different light sources that are operating simultaneously, and to track directions from which the light signals (after being reflected from the user's eye) are incident upon the individual light sensors. This is feasible because the light signals emitted by the different light sources have different coding. Such a code-division multiplexing is commonly used in IR-based transmissions.

Once the light direction and the light intensities of the light signals are known to the at least one processor, the orientation of the user's eye with respect to the given light-sensing unit can be easily determined by the at least one processor. It will be appreciated that the light intensities of the light signals are taken into account by the at least one processor for determining the orientation of the user's eye, because different parts of a surface of the user's eye reflect the light signals differently. In particular, scleral reflection is diffuse due to an uneven surface of a sclera of the user's eye, and corneal reflection is specular as a cornea of the user's eye behaves like a convex spherical mirror. Therefore, in cases where the light intensities are maximum, the user's eye could be determined to be oriented towards the given light-sensing unit, because the cornea of the eye is more reflective than the sclera. In other cases where the light intensities are less than the maximum, the orientation of the user's eye is determined to be away from the given light-sensing unit. In such cases, the orientation of the user's eye can be determined based on the light direction and the distribution of the light intensities across the at least three light sensors. It will be appreciated that the at least one processor is optionally configured to determine the orientation of the user's eye, further based on knowledge of how an eye geometry of the user's eye affects an angle of reflectance of the light signals incident upon the surface of the user's eye. It is to be understood that the orientation of the user's eye refers to an orientation of an imaginary line joining a centroid of the user's eye and a pupil of the user's eye and extending in an outward direction from the user's eye.

Notably, different orientations of the user's eye correspond to different gaze directions of the user's eye. Once the orientation of the user's eye is known to the at least one processor, the gaze direction of the user's eye can be easily determined by the at least one processor, because the user's eye is oriented along the gaze direction of the user's eye. As an example, when the orientation of the user's eye is towards a left side of the user's eye, the gaze direction of the user's eye is towards a left side of a field of view of the user's eye. In addition to this, when it is known (or even approximately known) to the at least one processor that how close or far the given light-sensing unit is arranged with respect to the user's eye, the at least one processor could ignore or take into account some of the light signals corresponding to the given light-sensing unit for subsequently determining the gaze direction of the user's eye, as described later. In this regard, when the plurality of light-sensing units are arranged at fixed positions (for example, at a periphery) in the apparatus comprising the eye-tracking system, the position of the given light-sensing unit relative to the user's eye is readily known to the at least one processor. However, the position of the given light-sensing unit relative to the user's eye may be known only approximately, because a distance between the user's eye and the given light-sensing unit may vary for different users as the different users have different eye configurations (for example, in terms of different vertex distances, different interpupillary distances, and the like), or may vary even for a same user due to relative movement of the eye-tracking system with respect to the user's eye during use. This may lead to variations in relative positions of the given light-sensing unit.

In an embodiment, the at least three light sensors are arranged according to a predefined arrangement, wherein the at least one processor is configured to determine the direction from which the light signals are incident upon the given light-sensing unit at the given instant of time, further based on at least one of: a diameter of a converging lens of the given light-sensing unit, a distance between the converging lens and the individual light sensors, a relative position of at least one of the individual light sensors that sensed a maximum light intensity with respect to a centroid of the predefined arrangement, weights corresponding to the light intensities of the light signals sensed by the individual light sensors.

In this regard, when at least one of: the diameter of the converging lens, the distance between the converging lens and the individual light sensors, the relative position of the at least one of the individual light sensors that sensed the maximum light intensity with respect to the centroid of the predefined arrangement is known to the at least one processor, the light direction could be easily ascertained by the at least one processor by employing at least a trigonometry-based function (for example, such as a sine or a cosine trigonometric function). It will be appreciated that the aforesaid light direction may lie along an imaginary line joining a centre of the converging lens and a centre of the at least one of the individual light sensors. It will be appreciated that the centroid of the predefined arrangement coincides with the centre of the converging lens, i.e., the converging lens is symmetrically arranged in front of the predefined arrangement of the at least three light sensors. Therefore, a distance between the centroid of the predefined arrangement and the centre of the converging lens could be readily known from the separation distance between the light sensors and the converging lens.

Furthermore, when there is no considerable difference between the light intensities of the light signals sensed by the individual light sensors, the light direction could be interpolated by using the weights corresponding to the light intensities of the light signals sensed by the individual light sensors. As an example, the given light-sensing unit may comprise four light sensors S1, S2, S3, and S4 such that the four light sensors S1-S4 are arranged towards a north direction, an east direction, a south direction, and a west direction, respectively. Light intensities of the light signals sensed by the four light sensors S1-S4 may be 100, 101, 102, and 101 units, respectively. Herein, since there is no considerable difference between the light intensities of the light signals, almost similar weights (for example, lying in a range from 0 to 1) could be assigned to the light intensity corresponding to each of the four light sensors S1-S4. In such a case, the light signals are determined to be incident upon the given light-sensing unit from a direction passing through the centre of the converging lens and the centroid of the arrangement of the four light sensors S1-S4. However, in the above example, if the aforesaid weights were not considered and rather the relative position of the at least one of the individual light sensors that sensed the maximum light intensity were considered, the light signals would have been incorrectly determined to be incident upon the given light-sensing unit from a north direction, that is opposite to the south direction where S3 is arranged relative to the centroid of the arrangement of light sensors.

Optionally, the predefined arrangement is one of: a triangular arrangement, a rectangular arrangement, a hexagonal arrangement. In this regard, the triangular arrangement includes a minimum of three light sensors arranged in a form of a triangle. The rectangular arrangement may include a 2×2 arrangement of light sensors, a 3×2 arrangement of light sensors, a 3×3 arrangement of light sensors, a 4×4 arrangement of light sensors, 4×5 arrangement of light sensors, or the like. The hexagonal arrangement includes a minimum of seven light sensors arranged in a form of a hexagon. The technical benefit of arranging the at least three light sensors according to any of the aforesaid predefined arrangements is that a centroid of any of the aforesaid predefined arrangements could be easily and accurately determined by the at least one processor, for subsequently determining the light direction. Moreover, the aforesaid predefined arrangements are simple, and easy to implement.

Optionally, the at least one processor is configured to:
predict, based on the position of the given light-sensing unit relative to the user's eye, a direction from which the light signals are expected to be incident upon the given light-sensing unit after being reflected from the user's eye;
ignore any of the light signals sensed by the individual light sensors that do not correspond to the predicted direction from which the light signals are expected to be incident;
select a remaining of the light signals sensed by the individual light sensors that correspond to the predicted direction from which the light signals are expected to be incident; and
determine the direction from which the light signals are incident upon the given light-sensing unit at the given instant of time, based on the remaining of the light signals sensed by the individual light sensors.

In this regard, since the position of the given light-sensing unit relative to the user's eye is (approximately) known to the at least one processor (as discussed earlier), the at least one processor could easily predict the direction from which the light signals are expected to be incident upon the given light-sensing unit after being reflected from the user's eye. As an example, when the given light-sensing unit is arranged towards a right side of the user's eye, the light signals may be expected to be incident from a left side of the given light-sensing unit. Moreover, light signals that do not correspond to the predicted direction are not useful for determining the (actual) direction from which the light signals are incident upon the given light-sensing unit, as said light signals may, for example, be reflecting from other parts of the eye socket of the user's eye. Therefore, the at least one processor filters out (namely, ignores or discards) such light signals, and considers only the remaining of the light signals for determining the light direction. In this regard, the aforesaid light direction is determined based on differences in light intensities of the remaining of the light signals sensed by the individual light sensors. This enables the eye-tracking method to achieve a high signal-to-noise ratio. Beneficially, such a manner of determining the light direction facilitates in accurate eye tracking.

It will be appreciated that the light direction could also be determined by implementing analog signal processing techniques. Such techniques may employ comparators and/or differential amplifiers for determining the differences in the respective light intensities of the individual sensors. Said techniques may employ at least one of: an analog-to-digital converter, an analog multiplexer, a simple state machine. Such an implementation scales very well with the number of light sensors in a given light-sensing unit.

Optionally, the at least one processor is configured to:
determine a correlation between different orientations of the user's eye relative to the given light-sensing unit and respective gaze directions of the user's eye, during an initial calibration of the eye-tracking system for the user's eye; and
utilise the correlation between the different orientations of the user's eye relative to the given light-sensing unit and the respective gaze directions of the user's eye, when determining the gaze direction of the user's eye.

In this regard, in order to be able to determine the gaze direction of the user's eye from the orientation of the user's eye relative to the given light-sensing unit, the correlation (between different orientations of the user's eye and different gaze directions) is required to be known beforehand, and thus the initial calibration of the eye-tracking system is performed.

In an example, during the initial calibration, the user may be required to wear a wearable device that comprises the eye-tracking system, and to view at least one reference image displayed on a display of the wearable device (or to view at least one reference image displayed on an external display through the wearable device). Herein, the term "reference image" refers to an image that is to be used for calibrating the eye-tracking system for the user's eye. Optionally, in this regard, the at least one reference image presents to the user a given visual target at a given location on the display or the external display. The term "visual target" refers to a visible mark that is represented within the at least one reference image and is distinctly visible in the at least one reference image. Different locations of the given visual target correspond to the different orientations of the user's eye and the respective gaze directions of the user's eye. The given visual target could be represented, for example, at a central portion, a corner portion, a top portion, a right side portion, a left side portion, and the like, within the at least one reference image. As an example, when the given visual target is at the central portion within the at least one reference image, the at least one processor could easily ascertain that an orientation of the user's eye would be towards a centre of the user's eye, and thus a gaze of the user's eye would be towards a central region of a field of view of the user's eye. As another example, when the given visual target is at the right side portion within the at least one reference image, the at least one processor could easily ascertain that an orientation of the user's eye would be towards a right side of the user's eye, and thus the gaze direction of the user's eye would be towards a right side region of a field of view of the user's eye. Since the at least one processor controls displaying of the at least one reference image, the given location of the given visual target is readily known to the at least one processor. In this regard, the at least one processor is configured to determine the correlation between the different orientations of the user's eye and the respective gaze directions of the user's eye, based on the given location of the given visual target. In this way, the at least one processor utilises the correlation for determining the gaze directions of the user's eye. The wearable device could be, for example, such as a pair of eye-glasses, a head-mounted display (HMD) device, and the like.

In another example, during the initial calibration, the user may be required to wear the wearable device comprising the eye-tracking system, and to focus on the given visual target represented within the at least one reference image while rotating his/her head. In yet another example, the calibration is not performed prior to using the eye-tracking system, but is performed during use of the wearable device comprising the eye-tracking system. In such a case, an initial error in the (determined) gaze direction may be high, but errors in subsequently determined gaze directions would be minimal. Moreover, a machine learning model may also be employed by the at least one processor to determine (and subsequently utilise) the correlation between the different orientations of the user's eye and the respective gaze directions of the user's eye.

Moreover, optionally, the eye-tracking system further comprises a plurality of light sources, wherein a given light source is to be employed to emit the light signals towards the user's eye. Herein, the term "light source" refers to an equipment that, in operation, emits the light signals. Examples of the given light source include, but are not limited to, a light-emitting diode (LED), a projector, a display, a laser. The laser may be a vertical-cavity surface-emitting laser (VCSEL), an edge-emitting laser (EEL), or the like. Optionally, the light signals are IR light signals. In other words, the given light source and the at least three light sensors optionally operate on IR light and can be implemented as a given IR light source and at least three IR light sensors. It will be appreciated that the IR light signals (or near-IR light signals) are invisible (or imperceptible) to a human eye, thereby reducing unwanted distraction when such light signals are incident upon the user's eye for eye-tracking purposes. This subsequently facilitates in determining the gaze direction of the user's eye with high accuracy. Alternatively, optionally, the light signals are visible light signals. Yet alternatively, optionally, the light signals are UV light signals. In such a case, the at least one light source and the at least three light sensors optionally operate on UV light and can be implemented as a given UV light source and at least three UV light sensors. In this regard, the UV light that is in a range of wavelengths which are not harmful to the human eye is selected. For example, a wavelength of the selected UV light may lie in a range from 315 nanometres to 400 nanometres.

Optionally, a given light source is fixedly arranged in the eye-tracking system in a manner that the given light source emits the light signals towards the user's eye in a fixed direction. In this regard, the at least one processor need not necessarily be configured to control the plurality of light sources for emitting the light signals towards the user's eye. Thus, emission of said light signals from the plurality of light sources could be implemented by using an analog signal feedback, for example, such as in servo control. Such an implementation is typically very fast, and is simple in construction. Moreover, in such a case, the given light source could be easily employed to operate in sync with the given light-sensing unit.

Alternatively, optionally, the at least one processor is configured to:
  determine at least one of the plurality of light sources that is to be employed to emit the light signals towards the user's eye when the given light-sensing unit is to be employed to sense the light intensities of the light signals upon reflection from the user's eye; and
  control the at least one of the plurality of light sources and the given light-sensing unit to operate in synchronisation.

In this regard, the at least one processor is optionally configured to control the at least one of the plurality of light sources for emitting the light signals towards the user's eye. In such a case, the at least one processor could readily and accurately determine which light source (from amongst the plurality of light sources) is to be employed to emit the light signals towards the user's eye. Such a determination can be done during an initial calibration of the eye-tracking system for the user's eye. In the initial calibration, it is ascertained beforehand that which light source(s) (from amongst the plurality of light sources) could be employed to emit the light signals towards the user's eye when the given light-sensing unit is to be employed to sense the light intensities of the light signals upon reflection from the user's eye.

Optionally, when the at least one of the plurality of light sources and the given light-sensing unit operate in synchronisation, the individual sensors (of the given light-sensing unit) are activated to collect the sensor data as soon as the at least one of the plurality of light sources emit the light signals towards the user's eye. The technical benefit of the aforesaid synchronisation is that an accuracy of eye tracking is improved as the direction from which the light signals are expected to be incident upon the given light-sensing unit (or particularly, the individual light sensors) is already known to the at least one processor, and thus the sensor data (indicative of the light intensities of the light signals) could be collected accurately (i.e., with minimal errors).

It will be appreciated that when the at least one of the plurality of light sources are controlled to operate in synchronisation with the given light-sensing unit, a direction of light signals emitted from the at least one of the plurality of light sources could be adjusted, by the at least one processor, using means for changing the direction of the light signals emitted by the at least one of the plurality of light sources. The aforesaid means is controlled (by the at least one processor) to steer the light signals, i.e., to change an optical path of the light signals for changing the direction of the light signals to scan the user's eye. In an embodiment, the aforesaid means is implemented as a liquid crystal (LC) lens arranged in front of a light-emitting surface of the at least one of the plurality of light sources to change the direction of the light signals. Such LC lenses are well-known in the art. In another embodiment, the aforesaid means is implemented as an actuator that is employed to adjust at least an orientation of the at least one of the plurality of light sources for changing the direction of the light signals. The term "actuator" refers to an equipment that is employed to rotate and/or tilt the at least one of the plurality of light sources to which it is connected (directly or indirectly). Such an actuator may, for example, include electrical components, mechanical components, magnetic components, polymeric components, and the like.

It will also be appreciated that the plurality of light-sensing units are controlled to operate in a time-division multiplexed manner. In such a case, the plurality of light-sensing units are interleaved in a manner that respective light-sensing units are well-synchronized with each other with respect to their operations, and thus do not interfere with each other during their operations. The term "time-division multiplexing" refers to a time-based interleaving of the plurality of light-sensing units, wherein a given light sensor senses the light signals in a given time slot and/or at a given framerate only.

Additionally, optionally, the at least one processor is configured to:
  determine a direction in which the at least one of the plurality of light sources is to emit the light signals towards the user's eye when the given light-sensing unit is to be employed to sense the light intensities of the light signals upon reflection from the user's eye; and
  control the at least one of the plurality of light sources to emit the light signals in the determined direction.

In this regard, once the at least one of the plurality of light sources is determined, it is required by the at least one processor to ascertain that in which direction the at least one of the plurality of light sources must emit the light signals towards the user's eye so that the given light-sensing unit could accurately sense the light intensities of the light signals upon reflection from the user's eye. The at least one of the plurality of light sources could possibly emit the light signals in any direction, but when the at least one of the plurality of light sources emits the light signals in a particular direction (i.e., the determined direction), it is ensured that the light signals (which are emitted towards the user's eye) upon reflecting from the user's eye reaches the given light-sensing unit. In this way, the sensor data could be reliably collected by the given light-sensing unit with high accuracy. Moreover, for multiple light-sensing units, a single light source (from amongst the plurality of light sources) is optionally employed to emit the light signals towards the user's eye. In this regard, an orientation of the single light source is adjusted in a manner that the direction of the light signals is changed at respective instants of time according to respective positions of the multiple light-sensing units. In such a case, the at least one processor ascertains more than one direction in which the single light source is to emit the light signals towards the user's eye at different instants of time, for the multiple light-sensing units.

It will be appreciated that the aforesaid determination of direction can be done during an initial calibration of the eye-tracking system for the user's eye. In the initial calibration, it is ascertained beforehand that in which direction(s) the light source(s) would emit the light signals towards the user's eye when the given light-sensing unit is to be employed to sense the light intensities of the light signals upon reflection from the user's eye.

The present disclosure also relates to the apparatus as described above. Various embodiments and variants disclosed above, with respect to the aforementioned first aspect, apply mutatis mutandis to the apparatus.

The apparatus implementing the eye-tracking system could, for example, be an eyeglass, a head-mounted display (HMD), a microscope, a telescope, a camera, or similar. Herein, the term "head-mounted display" device refers to an equipment that presents an extended-reality (XR) environment to a user when said HMD device, in operation, is worn by the user on his/her head. The HMD device is implemented, for example, as an XR headset, a pair of XR glasses, and the like, that is operable to display a visual scene of an XR environment to the user.

The at least one lens could be a concave lens, a convex lens, a bifocal lens, a liquid crystal lens, a Fresnel lens, a liquid crystal Fresnel lens or the like. Since eye tracking is to be performed for the user's eye when the apparatus is used by the user, the first surface of the at least one lens faces the user's eye. It will be appreciated that arranging the plurality of light-emitting units and optionally the plurality of light sensors along or in the proximity of the periphery of the first surface of the at least one lens facilitates in emitting the light beams towards the user's eye, and sensing the light beams after being reflected from the user's eye for accurate eye tracking.

The present disclosure also relates to the method as described above. Various embodiments and variants disclosed above, with respect to the aforementioned first aspect, apply mutatis mutandis to the method.

Optionally, the at least three light sensors are arranged according to a predefined arrangement, wherein the method further comprises determining the direction from which the light signals are incident upon the given light-sensing unit at the given instant of time, further based on at least one of: a diameter of a converging lens of the given light-sensing unit, a distance between the converging lens and the individual light sensors, a relative position of at least one of the individual light sensors that sensed a maximum light intensity with respect to a centroid of the predefined arrangement, weights corresponding to the light intensities of the light signals sensed by the individual light sensors.

Optionally, in the method, the predefined arrangement is one of: a triangular arrangement, a rectangular arrangement, a hexagonal arrangement.

Optionally, the method further comprises:
  predicting, based on the position of the given light-sensing unit relative to the user's eye, a direction from which the light signals are expected to be incident upon the given light-sensing unit after being reflected from the user's eye;
  ignoring any of the light signals sensed by the individual light sensors that do not correspond to the predicted direction from which the light signals are expected to be incident;
  selecting a remaining of the light signals sensed by the individual light sensors that correspond to the predicted direction from which the light signals are expected to be incident; and determining the direction from which the light signals are incident upon the given light-sensing unit at the given instant of time, based on the remaining of the light signals sensed by the individual light sensors.

Optionally, the method further comprises:

determining a correlation between different orientations of the user's eye relative to the given light-sensing unit and respective gaze directions of the user's eye, during an initial calibration of the eye-tracking system for the user's eye; and utilising the correlation between the different orientations of the user's eye relative to the given light-sensing unit and the respective gaze directions of the user's eye, when determining the gaze direction of the user's eye.

Optionally, the eye-tracking system further comprises a plurality of light sources, wherein a given light source is employed to emit the light signals towards the user's eye.

Optionally, the method further comprises:

determining at least one of the plurality of light sources that is to be employed to emit the light signals towards the user's eye when the given light-sensing unit is to be employed to sense the light intensities of the light signals upon reflection from the user's eye; and controlling the at least one of the plurality of light sources and the given light-sensing unit to operate in synchronisation.

Optionally, the method further comprises:

determining a direction in which the at least one of the plurality of light sources is to emit the light signals towards the user's eye when the given light-sensing unit is to be employed to sense the light intensities of the light signals upon reflection from the user's eye; and controlling the at least one of the plurality of light sources to emit the light signals in the determined direction.

DETAILED DESCRIPTION OF THE DRAWINGS

Figure 1B:
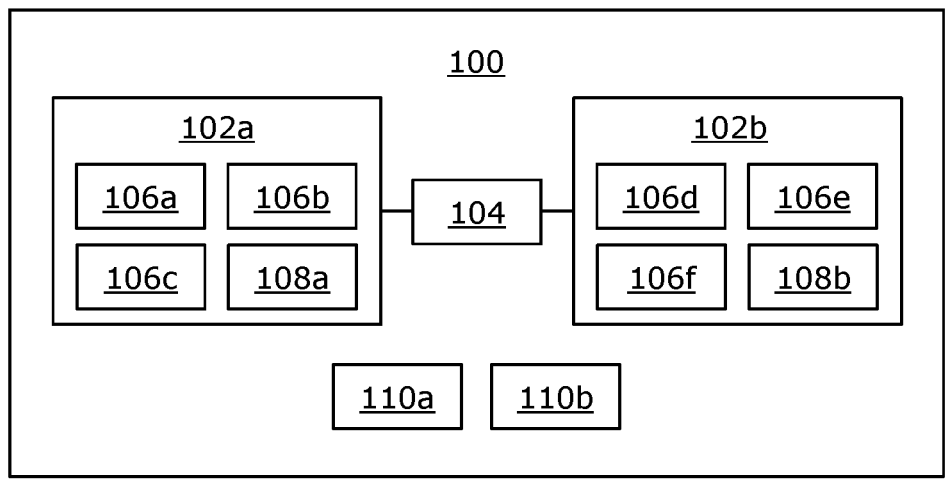

Referring to FIGS. 1A and 1B, illustrated are block diagrams of architectures of an eye-tracking system 100, in accordance with different embodiments of the present disclosure. In FIGS. 1A and 1B, the eye-tracking system 100 comprises a plurality of light-sensing units (depicted as light-sensing units 102a and 102b) and at least one processor (depicted as a processor 104). Each light-sensing unit 102a-b comprises at least three light sensors (depicted as light sensors 106a, 106b, and 106c of the light-sensing unit 102a and light sensors 106d, 106e, and 106f of the light-sensing unit 102b) and a converging lens (depicted as converging lenses 108a and 108b of the light-sensing units 102a and 102b, respectively). The processor 104 is communicably coupled to the light-sensing units 102a-b. With reference to FIG. 1B, the eye-tracking system 100 optionally comprises a plurality of light sources (depicted as light sources 110a and 110b). The light sources 110a-b may or may not be communicably coupled to the processor 104.

It may be understood by a person skilled in the art that FIGS. 1A and 1B include simplified architectures of the eye-tracking system 100 for sake of clarity, which should not unduly limit the scope of the claims herein. It is to be understood that the specific implementations of the eye-tracking system 100 are provided as examples and are not to be construed as limiting it to specific numbers of light-sensing units and light sensors. A person skilled in the art will recognize many variations, alternatives, and modifications of embodiments of the present disclosure.

Figure 2:
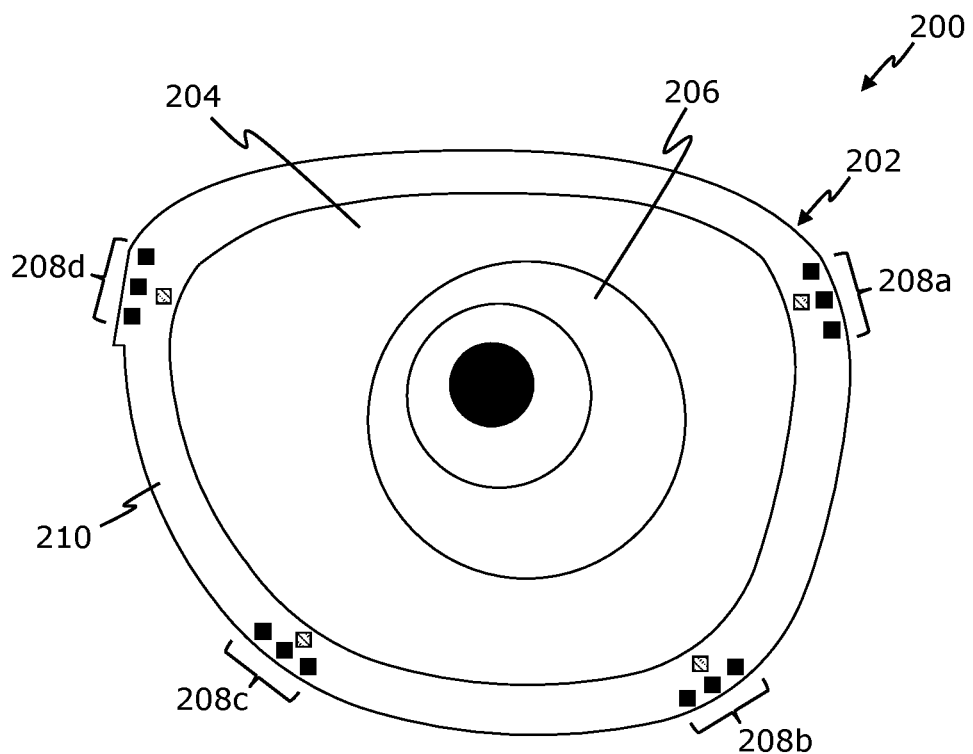
FIG. 2 illustrates a schematic diagram of a part of an apparatus in which an eye-tracking system is implemented, in accordance with an embodiment of the present disclosure.

Referring to FIG. 2, illustrated is a schematic diagram of a part of an apparatus 200 in which an eye-tracking system 202 is implemented, in accordance with an embodiment of the present disclosure. The apparatus 200 comprises at least one lens (depicted as a lens 204), wherein a first surface (not shown) of the lens 204 is to face a user's eye 206 when the apparatus 200 is used by the user. The eye-tracking system 202 comprises a plurality of light-sensing units and at least one processor (not shown). Each light-sensing unit comprises at least three light sensors (depicted as solid squares) and a converging lens (depicted as a hatched square). The plurality of light-sensing units of the eye-tracking system 202 are arranged along or in a proximity of a periphery of the first surface of the at least one lens, for example, as shown. There are shown, for example, multiple groups 208a-d of constituent elements of the eye-tracking system 202 arranged along a periphery 210 of the first surface of the lens 204.

Figures 3A, 3B, 3C:
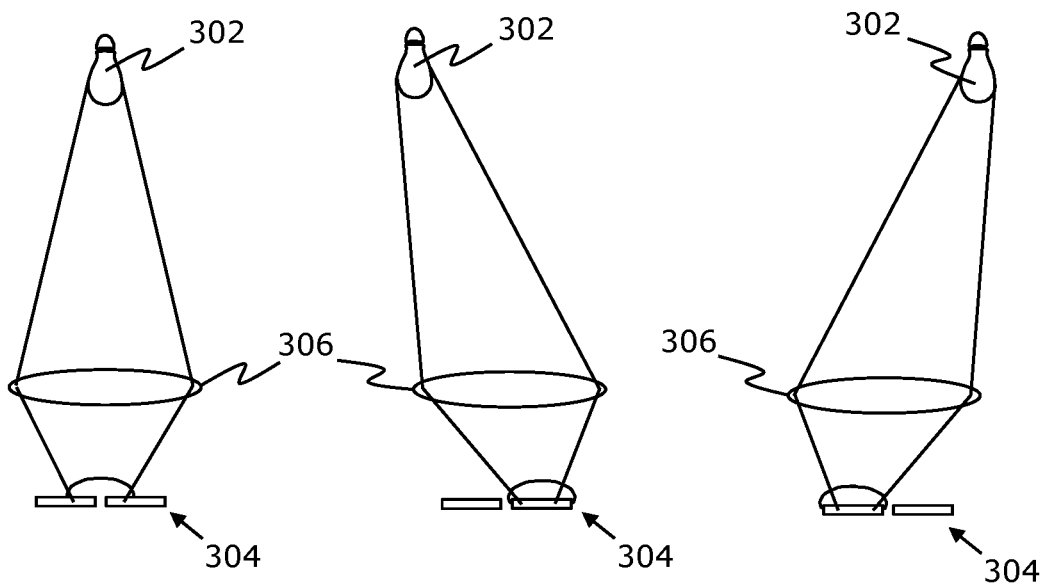
FIGS. 3A, 3B, and 3C illustrate various scenarios of incidence of light signals upon a light-sensing unit, in accordance with an embodiment of the present disclosure.

Referring to FIGS. 3A, 3B, and 3C, illustrated are various scenarios of incidence of light signals upon a light-sensing unit, in accordance with an embodiment of the present disclosure. In FIGS. 3A-3C, the light signals emitted by a light source 302 are shown to be incident upon a plurality of light sensors 304 of the light-sensing unit via a converging lens 306 arranged between an optical path of the light signals. For the sake of simplicity, only two light sensors of the plurality of light sensors 304 are shown in a one-dimensional manner. In FIG. 3A, a direction of the light signals is head-on with respect to the plurality of light sensors 304 such that each of the plurality of light sensors 304 senses (almost) equal light intensity of the light signals. In FIGS. 3B and 3C, a direction of the light signals is such that one of the plurality of light sensors 304 (for example, a light sensor arranged on a right side of the plurality of light sensors 304 in FIG. 3B, and a light sensor arranged on a left side of the plurality of light sensors 304 in FIG. 3C) senses a greater light intensity of the light signals as compared to remaining light sensors of the plurality of light sensors 304.

Referring to FIGS. 4A, 4B, 4C, and 4D, illustrated are various predefined arrangements in which light sensors (depicted as squares) of a light-sensing unit are arranged, in accordance with an embodiment of the present disclosure. In FIG. 4A, three light sensors are shown to be arranged in a triangular arrangement. In FIG. 4B, four light sensors are shown to be arranged in a rectangular arrangement as a 2×2 grid. In FIG. 4C, nine light sensors are shown to be arranged in a rectangular arrangement as a 3×3 grid. In FIG. 4D, seven light sensors are shown to be arranged in a hexagonal arrangement.

Referring to FIG. 5, illustrated is an exemplary scenario of determining a direction from which light signals are incident upon a light-sensing unit 500, in accordance with an embodiment of the present disclosure. The light-sensing unit comprises nine light sensors 502a-i arranged in a rectangular arrangement as a 3×3 grid, and a converging lens (not shown). The converging lens is symmetrically arranged upon the rectangular arrangement of the nine light sensors 502a-i in a manner that a centroid 'Y' of the rectangular arrangement coincides with a centre (not shown) of the converging lens. In an example scenario, the light sensor 502c may, for example, sense a maximum light intensity of the light signals incident upon the light-sensing unit 500. In such a case, the direction from which the light signals are incident upon the light-sensing unit 500 can be determined based on a relative position of the light sensor 502c with respect to the centroid 'Y', and a distance between the centroid 'Y' and the centre of the converging lens, for example, using at least a trigonometric function.

Figure 6:
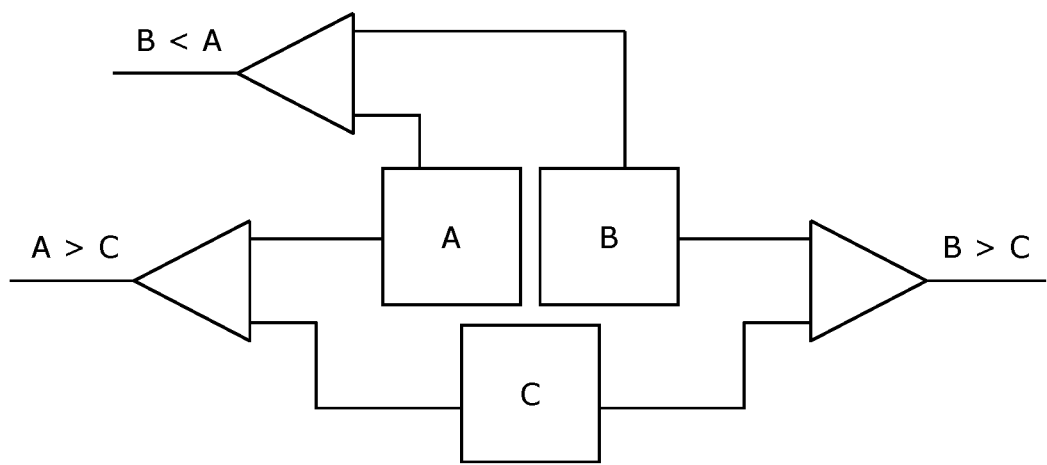
FIG. 6 illustrates an exemplary analog comparator for determining a direction from which light signals are incident upon a light-sensing unit, in accordance with an embodiment of the present disclosure.

Referring to FIG. 6, illustrated is an exemplary analog comparator for determining a direction from which light signals are incident upon a light-sensing unit, in accordance with an embodiment of the present disclosure. Herein, the analog comparator is shown using a circuit diagram. As shown, three light sensors A, B, and C (of the light-sensing unit) are arranged in a manner that relative differences of light intensities of the light signals sensed by any two light sensors from amongst the three light sensors A-C are utilized for determining the direction from which the light signals are incident upon the light-sensing unit. For example, for the light sensors A and B, an output of a corresponding sense amplifier enables in determining whether the light intensity of the light signals sensed by the light sensor A is greater than those sensed by the light sensor B. Similarly, for the light sensors B and C, an output of a corresponding sense amplifier enables in determining whether the light intensity of the light signals sensed by the light sensor B is greater than those sensed by the light sensor C. Likewise, for the light sensors A and C, an output of a corresponding sense amplifier enables in determining whether the light intensity of the light signals sensed by the light sensor A is greater than those sensed by the light sensor C. In this manner, output signals indicative of the relative differences are read out by scanning with the sense amplifiers coupled to analog-to-digital converters.

FIGS. 2, 3A-3C, 4A-4D, 5 and 6 are merely examples, which should not unduly limit the scope of the claims herein. The person skilled in the art will recognize many variations, alternatives, and modifications of embodiments of the present disclosure.

Figure 7:
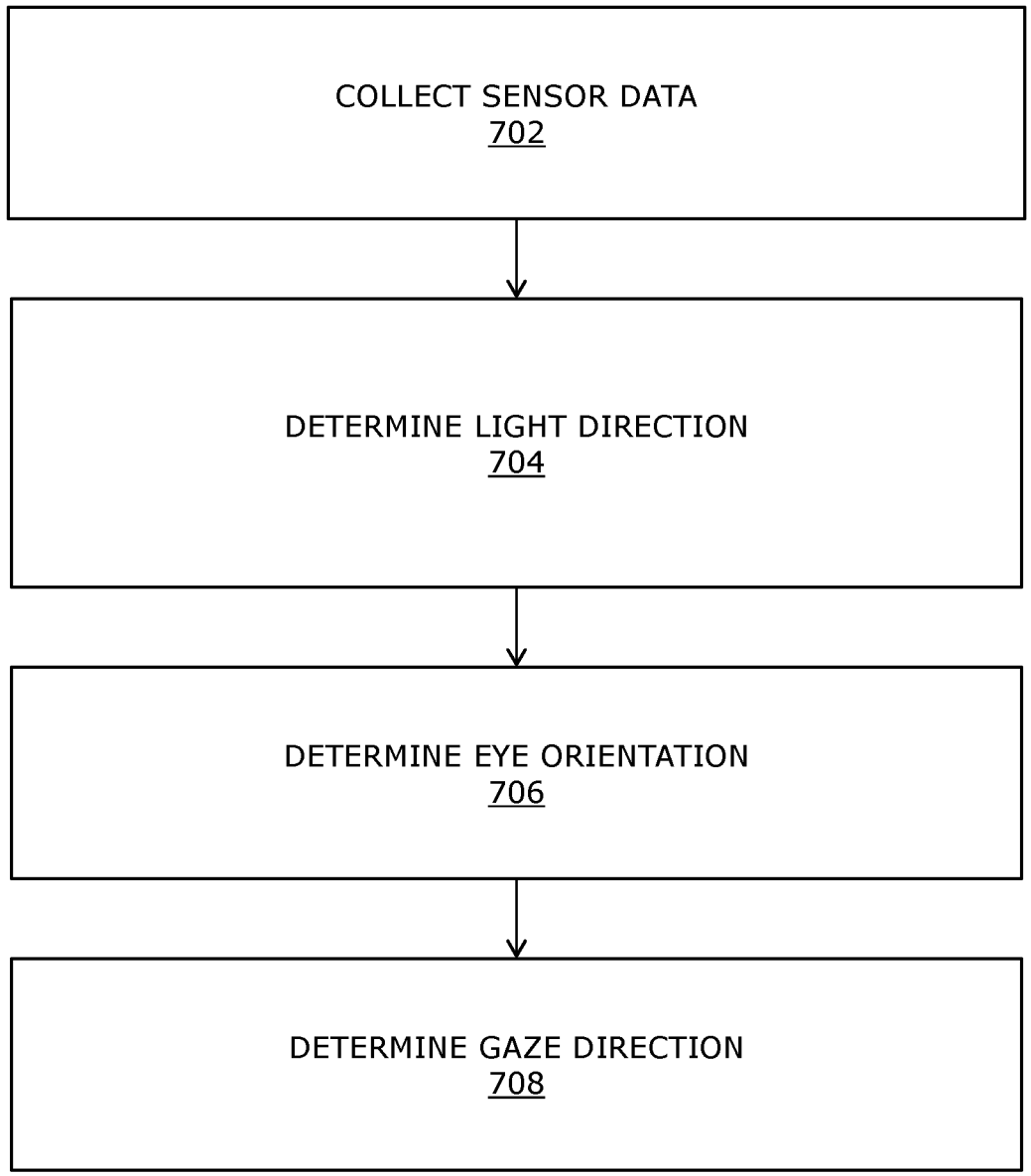
FIG. 7 illustrates steps of a method for eye tracking, in accordance with an embodiment of the present disclosure.

Referring to FIG. 7, illustrated are steps of a method for eye tracking, in accordance with an embodiment of the present disclosure. The method for eye-tracking uses an eye-tracking system comprising a plurality of light-sensing units, wherein each light-sensing unit comprises at least three light sensors and a converging lens employed to converge light signals incident thereupon towards one or more of the at least three light sensors. At step 702, sensor data is collected from individual light sensors of a given light-sensing unit at a given instant of time, the sensor data being indicative of respective light intensities of the light signals sensed by the individual light sensors. At step 704, a direction from which the light signals are incident upon the given light-sensing unit is determined at the given instant of time, based on differences in the respective light intensities of the light signals sensed by the individual light sensors. At step 706, an orientation of a user's eye is determined relative to the given light-sensing unit at the given instant of time, based on the direction from which the light signals are incident upon the given light-sensing unit and the light intensities of the light signals sensed by the individual light sensors. At step 708, a gaze direction of the user's eye is determined at the given instant of time, based on the orientation of the user's eye relative to the given light-sensing unit and a position of the given light-sensing unit relative to the user's eye.

The aforementioned steps are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An eye-tracking system comprising:
    a plurality of light-sensing units, each light-sensing unit comprising at least three light sensors and a converging lens employed to converge light signals incident thereupon towards one or more of the at least three light sensors; and
    at least one processor configured to:
    collect sensor data from individual light sensors of a given light-sensing unit at a given instant of time, the sensor data being indicative of respective light intensities of the light signals sensed by the individual light sensors;
    determine a direction from which the light signals are incident upon the given light-sensing unit at the given instant of time, based on differences in the respective light intensities of the light signals sensed by the individual light sensors;
    determine an orientation of a user's eye relative to the given light-sensing unit at the given instant of time, based on the direction from which the light signals are incident upon the given light-sensing unit and the light intensities of the light signals sensed by the individual light sensors; and
    determine a gaze direction of the user's eye at the given instant of time, based on the orientation of the user's eye relative to the given light-sensing unit and a position of the given light-sensing unit relative to the user's eye.

2. The eye-tracking system of claim 1, wherein the at least three light sensors are arranged according to a predefined arrangement, wherein the at least one processor is configured to determine the direction from which the light signals are incident upon the given light-sensing unit at the given instant of time, further based on at least one of: a diameter of a converging lens of the given light-sensing unit, a distance between the converging lens and the individual light sensors, a relative position of at least one of the individual light sensors that sensed a maximum light intensity with respect to a centroid of the predefined arrangement, weights corresponding to the light intensities of the light signals sensed by the individual light sensors.

3. The eye-tracking system of claim 2, wherein the predefined arrangement is one of: a triangular arrangement, a rectangular arrangement, a hexagonal arrangement.

4. The eye-tracking system of claim 1, wherein the at least one processor is configured to:
    predict, based on the position of the given light-sensing unit relative to the user's eye, a direction from which the light signals are expected to be incident upon the given light-sensing unit after being reflected from the user's eye;
    ignore any of the light signals sensed by the individual light sensors that do not correspond to the predicted direction from which the light signals are expected to be incident;
    select a remaining of the light signals sensed by the individual light sensors that correspond to the predicted direction from which the light signals are expected to be incident; and determine the direction from which the light signals are incident upon the given light-sensing unit at the given instant of time, based on the remaining of the light signals sensed by the individual light sensors.

5. The eye-tracking system of claim 1, wherein the at least one processor is configured to:
determine a correlation between different orientations of the user's eye relative to the given light-sensing unit and respective gaze directions of the user's eye, during an initial calibration of the eye-tracking system for the user's eye; and
utilise the correlation between the different orientations of the user's eye relative to the given light-sensing unit and the respective gaze directions of the user's eye, when determining the gaze direction of the user's eye.

6. The eye-tracking system of claim 1, further comprising a plurality of light sources, wherein a given light source is to be employed to emit the light signals towards the user's eye.

7. The eye-tracking system of claim 6, wherein the at least one processor is configured to:
determine at least one of the plurality of light sources that is to be employed to emit the light signals towards the user's eye when the given light-sensing unit is to be employed to sense the light intensities of the light signals upon reflection from the user's eye; and
control the at least one of the plurality of light sources and the given light-sensing unit to operate in synchronisation.

8. The eye-tracking system of claim 7, wherein the at least one processor is configured to:
determine a direction in which the at least one of the plurality of light sources is to emit the light signals towards the user's eye when the given light-sensing unit is to be employed to sense the light intensities of the light signals upon reflection from the user's eye; and
control the at least one of the plurality of light sources to emit the light signals in the determined direction.

9. An apparatus implementing the eye-tracking system of claim 1, comprising at least one lens, wherein a first surface of the at least one lens is to face the user's eye when the apparatus is used by the user, wherein the plurality of light-sensing units are arranged along or in proximity of a periphery of the first surface of the at least one lens.

10. A method for eye-tracking using an eye-tracking system comprising a plurality of light-sensing units, each light-sensing unit comprising at least three light sensors and a converging lens employed to converge light signals incident thereupon towards one or more of the at least three light sensors, the method comprising:
collecting sensor data from individual light sensors of a given light-sensing unit at a given instant of time, the sensor data being indicative of respective light intensities of the light signals sensed by the individual light sensors;
determining a direction from which the light signals are incident upon the given light-sensing unit at the given instant of time, based on differences in the respective light intensities of the light signals sensed by the individual light sensors;
determining an orientation of a user's eye relative to the given light-sensing unit at the given instant of time, based on the direction from which the light signals are incident upon the given light-sensing unit and the light intensities of the light signals sensed by the individual light sensors; and
determining a gaze direction of the user's eye at the given instant of time, based on the orientation of the user's eye relative to the given light-sensing unit and a position of the given light-sensing unit relative to the user's eye.

11. The method of claim 10, wherein the at least three light sensors are arranged according to a predefined arrangement, wherein the method further comprises determining the direction from which the light signals are incident upon the given light-sensing unit at the given instant of time, further based on at least one of: a diameter of a converging lens of the given light-sensing unit, a distance between the converging lens and the individual light sensors, a relative position of at least one of the individual light sensors that sensed a maximum light intensity with respect to a centroid of the predefined arrangement, weights corresponding to the light intensities of the light signals sensed by the individual light sensors.

12. The method of claim 11, wherein the predefined arrangement is one of: a triangular arrangement, a rectangular arrangement, a hexagonal arrangement.

13. The method of claim 10, further comprising:
predicting, based on the position of the given light-sensing unit relative to the user's eye, a direction from which the light signals are expected to be incident upon the given light-sensing unit after being reflected from the user's eye;
ignoring any of the light signals sensed by the individual light sensors that do not correspond to the predicted direction from which the light signals are expected to be incident;
selecting a remaining of the light signals sensed by the individual light sensors that correspond to the predicted direction from which the light signals are expected to be incident; and
determining the direction from which the light signals are incident upon the given light-sensing unit at the given instant of time, based on the remaining of the light signals sensed by the individual light sensors.

14. The method of claim 10, further comprising:
determining a correlation between different orientations of the user's eye relative to the given light-sensing unit and respective gaze directions of the user's eye, during an initial calibration of the eye-tracking system for the user's eye; and
utilising the correlation between the different orientations of the user's eye relative to the given light-sensing unit and the respective gaze directions of the user's eye, when determining the gaze direction of the user's eye.

15. The method of claim 10, wherein the eye-tracking system further comprises a plurality of light sources, wherein a given light source is employed to emit the light signals towards the user's eye.

16. The method of claim 15, further comprising:
determining at least one of the plurality of light sources that is to be employed to emit the light signals towards the user's eye when the given light-sensing unit is to be employed to sense the light intensities of the light signals upon reflection from the user's eye; and
controlling the at least one of the plurality of light sources and the given light-sensing unit to operate in synchronisation.

17. The method of claim 16, further comprising:
determining a direction in which the at least one of the plurality of light sources is to emit the light signals towards the user's eye when the given light-sensing unit is to be employed to sense the light intensities of the light signals upon reflection from the user's eye; and controlling the at least one of the plurality of light sources to emit the light signals in the determined direction.

* * * * *